(12) United States Patent
DeLuca et al.

(10) Patent No.: US 7,566,696 B2
(45) Date of Patent: *Jul. 28, 2009

(54) USE OF CALCITONIN AND CALCITONIN-LIKE PEPTIDES TO TREAT AND PREVENT MULTIPLE SCLEROSIS

(75) Inventors: Hector F. DeLuca, Deerfield, WI (US); Terrence F. Meehan, Encinitas, CA (US); Bryan R. Becklund, Madison, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 335 days.

This patent is subject to a terminal disclaimer.

(21) Appl. No.: 11/583,267

(22) Filed: Oct. 19, 2006

(65) Prior Publication Data
US 2007/0105774 A1    May 10, 2007

Related U.S. Application Data

(63) Continuation-in-part of application No. 10/235,244, filed on Sep. 5, 2002, and a continuation of application No. 11/352,717, filed on Feb. 13, 2006.

(60) Provisional application No. 60/652,831, filed on Feb. 14, 2005.

(51) Int. Cl.
*A61K 38/23* (2006.01)

(52) U.S. Cl. ............................... 514/12; 514/167

(58) Field of Classification Search .................. None
See application file for complete search history.

(56) References Cited

U.S. PATENT DOCUMENTS

| 5,614,513 | A | 3/1997 | Knutson |
| 5,716,946 | A | 2/1998 | DeLuca |
| 5,831,000 | A | 11/1998 | Murayama |
| 7,048,906 | B2 | 5/2006 | Lin |
| 2003/0207847 | A1 | 11/2003 | DeLuca |
| 2004/0053813 | A1 | 3/2004 | DeLuca |
| 2004/0146549 | A1 | 7/2004 | Ben-Sasson |
| 2004/0156826 | A1 | 8/2004 | Dangond |
| 2005/0009742 | A1 | 1/2005 | Bertilsson |

FOREIGN PATENT DOCUMENTS

AU         719773         5/2000

OTHER PUBLICATIONS

Rudinger, Peptide Hormones, JA Parsons, 1976, 1-7.*
T-Hart, DDT, 2004, 9(12), pp. 517-524.*
Lazar, Molecular and Cellular Biology, 1988, vol. 8, No. 3, pp. 1247-1252.*

* cited by examiner

*Primary Examiner*—Chritopher R. Tate
*Assistant Examiner*—Roy Teller
(74) *Attorney, Agent, or Firm*—Quarles & Brady LLP

(57) ABSTRACT

Methods for treating and preventing multiple sclerosis by administering to a patient an effective amount of calcitonin, calcitonin-like peptides or calcitonin mimetics to a patient. Additionally, 1,25-dihydroxyvitamin D analogs can be used in combination with the calcitonin, calcitonin-like peptides or calcitonin mimetics.

4 Claims, 6 Drawing Sheets

A.)

B.)

A.)

B.)

A.)

B.)

A.)

B.)

USE OF CALCITONIN AND CALCITONIN-LIKE PEPTIDES TO TREAT AND PREVENT MULTIPLE SCLEROSIS

CROSS-REFERENCE TO RELATED APPLICATIONS

This application is a continuation-in-part of U.S. application Ser. No. 10/235,244 filed Sep. 5, 2002 and is a continuation of U.S. application Ser. No. 11/352,717 filed Feb. 13, 2006 which claims the benefit of U.S. Provisional Application No. 60/652,831 filed Feb. 14, 2005, all of which are incorporated herein by reference as if set forth in their entirety.

STATEMENT REGARDING FEDERALLY SPONSORED RESEARCH OR DEVELOPMENT

Not applicable.

BACKGROUND

The invention relates generally to methods and compositions for treating and preventing multiple sclerosis, and more particularly to methods and compositions for treating and preventing multiple sclerosis by administration of synthetic calcitonin, calcitonin-like peptides or calcitonin mimetics to a patient.

Multiple Sclerosis

In multiple sclerosis (MS), inflammation of nervous tissue causes loss of myelin, a fatty material that acts as a protective insulation for nerve fibers in the brain and the spinal cord. This loss of myelin, or demyelination, leaves multiple areas of scar tissue, or sclerosis, along nerve cells. Consequently, the sclerosis results in multiple and varied neurological signs and symptoms, usually with repeated relapse and remission.

To date, treatment of MS has focused on the reduction of symptoms, which includes, but are not limited to, reduced or loss of vision, stumbling and uneven gait, slurred speech, as well as urinary frequency and incontinence. In addition, MS can cause mood changes and depression, muscle spasms and severe paralysis. The cause of MS is unknown, but an immunologic abnormality is suspected in causing the initial inflammation, with few clues presently indicating a specific mechanism (The Merck Manual, 16th Edition, 1993 Merck & Co.).

MS is more frequent at northern latitudes. Depending on the region in the Western world, the prevalence varies with 50-150 cases per 100,000 individuals. In the United States alone, some 250,000-350,000 individuals have an MS diagnosis. Females are twice as likely to develop MS when compared to males.

Current treatments for MS generally suppress the immune system. For example, one treatment includes transplantation of bone marrow along with administration of cytostatics and immunosupressive drugs. This treatment works for some patients, but it is expensive and includes several risks for patients. Additionally, the administration of cytostatics is considered controversial in treating MS because its effects are unclear and potential side-effects are severe.

Other treatments aim to cure or delay the MS disease. Among certain patients, interferon-beta (AVONEX™ and BETASERON™) reduces the symptoms of MS and is therefore administered to most patients for ethical reasons. Unfortunately, the mechanism of action of interferon-beta is unclear for these patients. Like suppressive treatments, interferon-beta is expensive. For other patients, glatiramer acetate (COPAXONE™) reduces the frequency of attacks; however, its side effects are substantial and problems occur in distinguishing the symptoms of MS from the side effects of glatiramer acetate.

The latest drug to be approved by the FDA for treatment for relapsing forms of MS is TYSABRI™ (NATALIZUMAB, formerly known as ANTEGREN). As noted above, most drugs for treating MS suppress the immune system. TYSABRI™, however, blocks immune cells from crossing into the central nervous system (CNS), thereby preventing damage to the nerves. One drawback of TYSABRI™ is its side effects, which include headache, fatigue, urinary tract infection, depression, lower respiratory tract infection, joint pain and abdominal discomfort. Another drawback with TYSABRI™ is that no long-term safety information is available.

Currently, an effective treatment for MS does not exist. Treatment is focused on merely reducing its symptoms. Tests with transplantation and different drug treatments to cure the disease have not demonstrated any solutions. Accordingly, a demand for drugs that can protect an MS patients from the severe development of the disease is therefore of high priority.

Calcitonin

In many instances, $1,25(OH)_2D_3$ only completely prevents EAE at doses that are likely to cause hypercalcemia, which leads to increased circulating levels of calcitonin. Furthermore, hypercalcemia independent of $1,25(OH)_2D_3$ can prevent EAE in female mice. Calcitonin has been shown to have anti-inflammatory properties in several animal models of inflammatory disease. Finally, calcitonin has also shown promise in treating the autoimmune disease rheumatoid arthritis.

Calcitonin is a thirty-two amino acid polypeptide hormone that participates in calcium and phosphorous metabolism. It is cleaved from a larger prohormone (approximately 15 kDa) and decreases serum calcium by inhibiting the reabsorption of calcium from bone and kidney. Calcitonin is synthesized in the parafollicular or C-cells in the thyroid gland in mammals, but it is also isolated from the ultimobrachial glands in birds, fish and amphibians.

A large number of diseases are associated with abnormally increased or decreased levels of calcitonin; however, pathologic effects of abnormal calcitonin secretion per se are not generally recognized. As such, calcitonin has several therapeutic uses. For one, it is used to treat hypercalcemia resulting from a number of causes. Additionally, calcitonin is a valuable therapy for Paget disease, which is a disorder in bone remodeling. Furthermore, it is a valuable aid in the management of certain types of osteoporosis.

Calcitonin has been obtained from several different species, including, but not limited to, bovine, eel, human, porcine, rat and salmon. In all of these species, the primary structure of calcitonin is similar, although some structural variations exist (see Table I). Of the thirty-two amino acids present in calcitonin, eight residues are conserved across all species. Additionally, calcitonins with amino acid sequences identical to the natural forms have been produced by chemical synthesis, as well as by recombinant technology.

TABLE I

Amino Acid Sequences of Calcitonin in Representative Species.

| Species | Amino Acid Sequence |
|---|---|
| Bovine | Cys-Ser-Asn-Leu-Ser-Thr-Cys-Val-Leu-Ser-Ala-Tyr-Trp-Lys-Asp-Leu-Asn-Asn-Tyr-His- |

TABLE I-continued

Amino Acid Sequences of Calcitonin
in Representative Species.

| Species | Amino Acid Sequence |
|---|---|
| | Arg-Phe-Ser-Gly-Met-Gly-Phe-Gly-Pro-Glu-Thr-Pro (SEQ ID NO: 1) |
| Eel | Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro (SEQ ID NO: 2) |
| Human | Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro (SEQ ID NO: 3) |
| Porcine | Cys-Ser-Asn-Leu-Ser-Thr-Cys-Val-Leu-Ser-Ala-Tyr-Trp-Arg-Asn-Leu-Asn-Asn-Phe-His-Arg-Phe-Ser-Gly-Met-Gly-Phe-Gly-Pro-Glu-Thr-Pro (SEQ ID NO: 4) |
| Rat | Cys-Gly-Asn-Leu-Ser-Thr-Cys-Met-Leu-Gly-Thr-Tyr-Thr-Gln-Asp-Leu-Asn-Lys-Phe-His-Thr-Phe-Pro-Gln-Thr-Ser-Ile-Gly-Val-Gly-Ala-Pro (SEQ ID NO: 5) |
| Salmon | Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro (SEQ ID NO: 6) |

Calcitonin has several important structural features. Salmon calcitonin, for example, has a disulphide bridge (cystine link) between the first and seventh amino acids at the amino end of the polypeptide chain. This disulphide bridge is essential for its biological activity as it causes the amino terminus to assume the shape of a ring. Additionally, salmon calcitonin has a prolinamide group at the carboxyl terminal amino acid. Alternative splicing of the calcitonin pre-mRNA can yield a mRNA encoding calcitonin gene-related peptide; this peptide appears to function in the nervous and vascular systems.

Interestingly, salmon calcitonin has been shown to be considerably more effective in arresting bone resorption than human forms of calcitonin. Several hypotheses have been offered to explain this observation and include the following: (1) salmon calcitonin is more resistant to degradation; (2) salmon calcitonin has a lower metabolic clearance rate (MCR); and (3) salmon calcitonin may have a slightly different conformation, resulting in a higher affinity for bone receptor sites.

Despite the advantages associated with the use of salmon calcitonin in humans, there are also disadvantages such as cost and limited method of administration (by injection). Additionally, resistance to calcitonin therapy may occur with long-term use. Furthermore, some patients develop antibodies to non-human calcitonin, calcitonin mimetics would be useful for such patients. Therefore, use of synthetic calcitonin, calcitonin-like peptides or calcitonin mimetics, either in place of native calcitonins or in rotation with native calcitonins, may help to avoid resistance to such treatment during long-term use.

Needed in the art of multiple sclerosis treatment is a method of effectively using calcitonin, possibly in combination with other multiple sclerosis treatments, as an effective therapeutic.

SUMMARY OF THE INVENTION

In one embodiment, the present invention is a method for decreasing multiple sclerosis symptoms comprising the steps of (a) selecting a multiple sclerosis patient or patient in danger of multiple sclerosis, and (b) administering an amount of calcitonin, calcitonin-like peptide or calcitonin mimetic to the patient, wherein the amount is sufficient to diminish multiple sclerosis symptoms. Preferably, the calcitonin is selected from the group consisting of human and salmon calcitonin and the patient is female.

In one embodiment, the method additionally comprising the step of administering an amount of 1,25-dihydroxyvitamin D analog effective to reduce multiple sclerosis symptoms.

Preferably, the vitamin D analog is a 1α, 25 vitamin D compound, preferably a 19-nor-vitamin D.

In another embodiment, the present invention is a pharmaceutical preparation comprising calcitonin, calcitonin-like-peptide or calcitonin mimetic combined with a 1,25-dihydroxyvitamin D analog in an amount effective to relieve multiple sclerosis symptoms.

Other objects, advantages and features of the present invention will become apparent after review of the specification, claims and drawings.

BRIEF DESCRIPTION OF THE DRAWINGS

The invention will be better understood and features, aspects and advantages other than those set forth above will become apparent when consideration is given to the following detailed description thereof. Such detailed description makes reference to the following drawings, wherein:

FIG. 1A diagrams mean EAE score versus days post immunization. FIG. 1B diagrams serum calcium versus days post immunization.

FIG. 2A diagrams mean EAE score versus days post immunization. FIG. 2B diagrams serum calcium versus days post immunization.

DETAILED DESCRIPTION OF THE PREFERRED INVENTION

Figure 1:
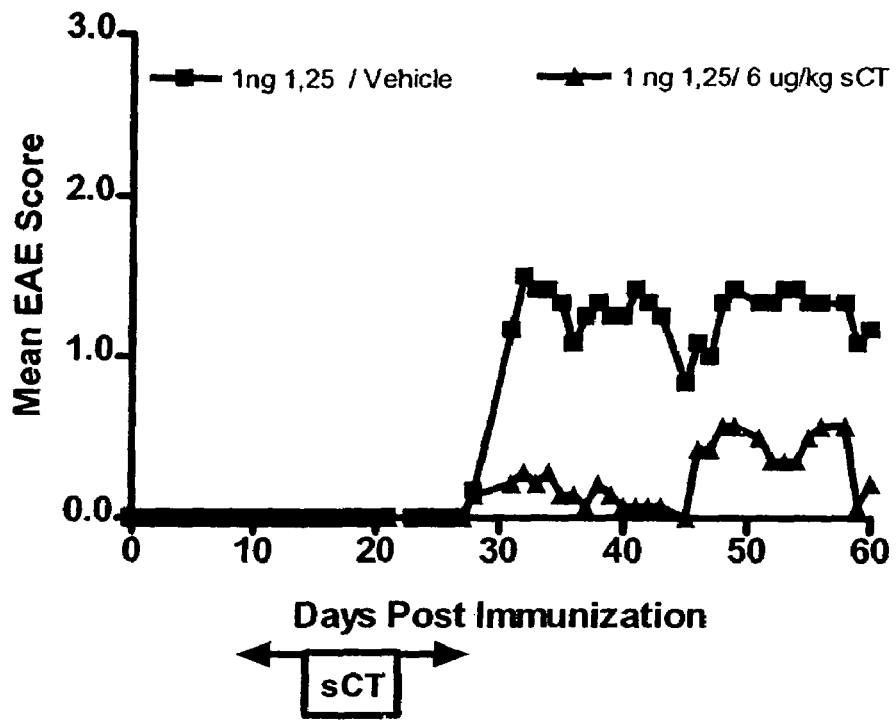
FIG. 1 is a set of graphs illustrating the effect of calcitonin on a murine model of MS, Experimental Autoimmune Encephalomyelitis (EAE). 25 hydroxyvitamin $D_3$-1α-hydroxylase knock out mice (1α-OH KO) were maintained on a purified diet containing 1 ng 1,25 $(OH)_2D_3$ for two to three weeks prior to EAE immunization. The graphs show the difference between mice who were and were not given 6 μg/kg sCT.
Figure 1:
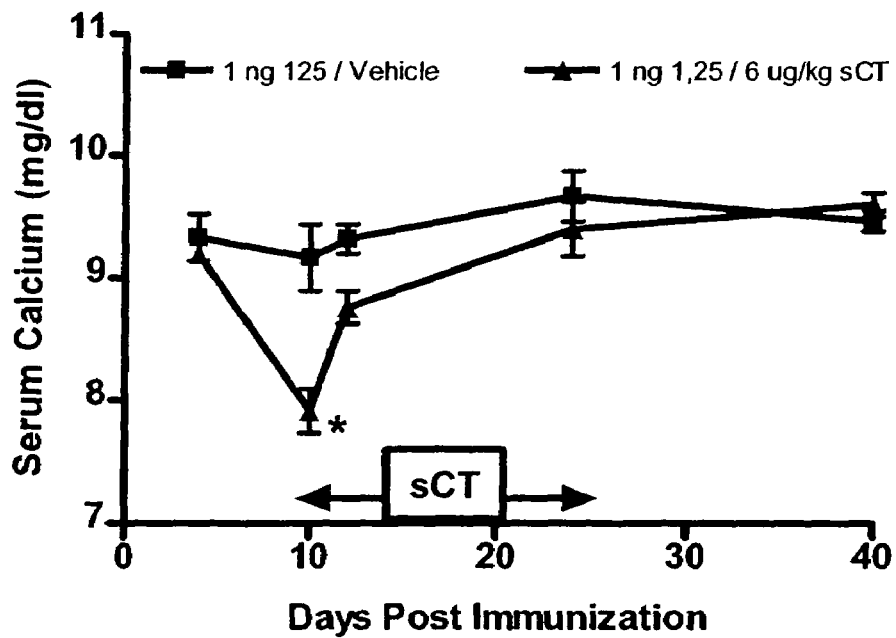

The present invention is the use of calcitonin, calcitonin-like peptides or calcitonin mimetics to treat and prevent MS symptoms. In some embodiments, one would combine vitamin D analogs, described below, with calcitonin for treatment and prevention of MS symptoms.

In general, the present invention envisions the selection of a MS patient or a patient who may be genetically or environmentally susceptible to MS and administration of a sufficient amount of calcitonin, a calcitonin-like peptide, or a calcitonin mimetic to that patient so that multiple sclerosis symptoms are diminished. Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

By "multiple sclerosis" or "MS," we mean an auto-immune disease of the CNS.

By "calcitonin," we mean to include native and synthetic calcitonins. For example, MIACALCIN® is a synthetic salmon calcitonin that is currently used as an injectable therapeutic for Paget's disease and bone physiology therapeutics, such as for the treatment of hypercalcemia and for the treatment of post-menopausal osteoporosis. MIACALCIN® would be a suitable type of calcitonin for use in the treatment and prevention of multiple sclerosis. Similarly, CALCIMAR® (Aventis Pharmaceutical Products, Inc.; Paris, France) is another injectable salmon calcitonin suitable for the present invention. CIBACALCIN™ (Novartis A G; Basel, Switzerland) is a synthetic human calcitonin suitable for the present invention. We mean to include calcitonin isolated from mammals, birds, fish, and amphibians or identical synthetic products.

By "calcitonin-like peptides," we mean native or synthetic peptides or peptide derivatives (such as ELCATONIN™, which is a calcitonin derivative derived from eel calcitonin by changing the S—S bond into the stable C—N bond). Calcitonin-like peptides, as the term is used herein, have at least 70% sequence similarity (with 100% identity in the eight conserved amino acids), and preferably at least 95% sequence similarity to the human or animal (preferably, salmon) calcitonin peptides described above and exhibit 95% of the therapeutic activity that calcitonin exhibits as demonstrated in the Examples below.

It is also envisioned that other types of calcitonins ("calcitonin-like peptides") may be applicable to the invention. These include: substituted salmon calcitonin (salcatonin) analogues (U.S. Pat. No. 6,107,277 assigned to Therapicon S. R. L.; Milan, Italy); hybrid calcitonin having a peptide segment from human calcitonin and a peptide segment from calcitonin derived from non-humans animals, such as eel, salmon and chicken. The hybrid calcitonin exhibits biological activities as strong as animal calcitonin without causing side effects in humans including nausea, disorders in the functions of the digestive tract or antigenicity (see U.S. Pat. No. 5,831,000 assigned to Chugai Seiyaku Kabushiki Kaisha; Tokyo, JP; and Asahi Glass Co., Ltd.; Tokyo, JP).

By "calcitonin mimetic," we mean native or synthetic compounds with the ability to mimic the effects generated by calcitonin's interaction with its receptor and, by such interaction, stimulate G-protein-mediated activation by adenylate cyclase. As a result, these compounds are useful in the treatment of diseases that are mediated by calcitonin. Included among the calcitonin mimetics of the present invention are piperazine derivatives in which each of the nitrogens in the piperazine ring are alkylated or acylated with substituted aryl groups (see U.S. Pat. Nos. 6,395,740; 5,698,521; 5,698,672 assigned to ZymoGenetics, Inc.; Seattle, Wash.).

Currently, calcitonins are mainly available in solution and are administered by intravenous infusion, by intramuscular injection, subcutaneously or intranasally. In order to maintain biological activity pharmaceutical preparations containing calcitonin is preferably stored at a temperature of 2° C. to 8° C. to slow down the extent of degradation. However, stable formulations oral calcitonin pharmaceutical compositions have recently been identified and may be suitable for use in the treatment of MS (see U.S. Pat. No. 6,352,974 assigned to Eurand International S.P.A.; Milan, IT).

We envision that dosages such as those given for commercially available calcitonin such as MIACALCIN® (Novartis A G; Basel, Switzerland) will be sufficient and suitable for the present invention. Similarly, it is envisioned that the dosage and treatment with calcitonin or calcitonin peptides will differ for different patients. It is noted that the number of doses a patient receives, the time allowed between doses, and the length of time a patience receives the medicine will generally depend on the severity of the MS symptoms.

It is envisioned that the quantity of pharmacologically active calcitonin in a unit dose will vary according to the potency of the calcitonin and the nature of the composition. However, in general, a unit dose of a composition intended for human use typically contains between 1 and 1000 International Units (I.U.) of a calcitonin. For human calcitonin, the dosage is between 100 to 1000 micrograms (µg). For salmon calcitonin a unit dose in general contains from 50 to 500 I.U., preferably 100 I.U. For ELCATONIN™ (Lipotech, S.A.; Buenos Aries, Argentina), a unit dose in general contains from 5 to 200 I.U. A unit dose adapted for colonic administration preferably contains from 40 to 800 I.U. of ELCATONIN™. The compositions will be administered to the patient in dosages that contain an amount of calcitonin effective to treat the disease in question.

For example, in a preferred embodiment, human calcitonin may be given to an adult patient in an injection dosage form starting at 500 µg injected under the skin once a day. This dosage level and the time between doses may be modified based on the physician's assessment of the disease progression.

In another embodiment, salmon calcitonin may be given to an adult patient in an injection dosage form starting at 100 I.U. injected into a muscle or under the skin once a day, once every other day, or three times a week. This dosage level and the time between doses may be modified based on the physician's assessment of the disease progression.

In yet another embodiment, a typical dosage regimen for ELCATONIN™ is from 5 to 200 I.U. per day (or 40 to 800 I.U. for colonic administration) which may be administered in a single dose or in divided doses for example on consecutive or alternate days. We envision that multiple forms of administration, such as injection, oral administration, skin patches and nasal administration, would be effective.

The patient would then be examined to determine whether multiple sclerosis symptoms such as those described above are reduced. Although the symptoms can be extremely varied and erratic, they may include tingling, numbness, loss of balance, weakness, double vision, fatigue, incontinence, paralysis, memory and speech difficulties.

In one preferred form of the present invention, one would treat the patient with both calcitonin, as described above, and 1,25-dihydroxyvitamin D analogs, for example, those analogs described for the treatment of multiple sclerosis in U.S. patent application Ser. No. 10/405,653 and U.S. Pat. No. 5,716,946, each of which is incorporated herein by reference as if set forth in its entirety. By the phrase "1,25-dihydroxyvitamin D analog" we specifically mean the compositions mentioned in paragraphs [00046] through [00050] in this application.

For example, one would wish to use the following 1,25-dihydrozyvitamin D analogs:

In a particularly advantageous form of the reaction, the administered compound is either 1α,25-dihydroxyvitamin $D_3$ (1,25-$(OH)_2D_3$), 19-nor-1,25-dihydroxyvitamin $D_2$ (19-nor-1,25-$(OH)_2D_3$), 24-homo-22-dehydro-22E-1α,25-dihydroxyvitamin $D_3$ (24-homo-22-dehydro-22E-1,25-$(OH)_2$ $D_3$), 1,25-dihydroxy-24(E)-dehydro-24-homo-vitamin $D_3$ (1,25-$(OH)_2$-24-homo $D_3$), or 19-nor-1,25-dihydroxy-21-epi-vitamin $D_3$ (19-nor-1,25-$(OH)_2$-21-epi-$D_3$).

In another form of the present invention, the vitamin D compound has the formula

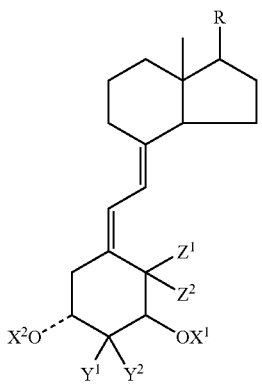

wherein $X^1$ and $X^2$ are each selected from the group consisting of hydrogen and acyl; wherein $Y^1$ and $Y^2$ can be H, or one can be 0-aryl, 0-alkyl, aryl, alkyl of 1-4 carbons, taken together to form an alkene having the structure of

where $B_1$ and $B_2$ can be selected from the group consisting of H, alkyl of 1-4 carbons and aryl, and can have a β or α configuration; $Z^1=Z^2$=H or $Z^1$ and $Z^2$ together are =$CH_2$; and wherein R is an alkyl, hydroxyalkyl or fluoroalkyl group, or R may represent the following side chain:

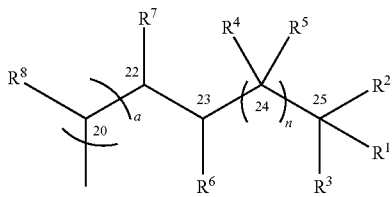

wherein (a) may have an S or R configuration, $R^1$ represents hydrogen, hydroxyl or O-acyl, $R^2$ and $R^3$ are each selected from the group consisting of alkyl, hydroxyalkyl and fluoralkyl, or, when taken together represent the group-$(CH_2)_m$- wherein m is an integer having a value of from 2 to 5, $R^4$ is selected from the group consisting of hydrogen, hydroxyl, fluorine, O-acyl, alkyl, hydroxyalkyl and fluoralkyl, wherein if $R^5$ is hydroxyl or fluoro, $R^4$ must be hydrogen or alkyl, R5 is selected from the group consisting of hydrogen, hydroxyl, fluorine, alkyl, hydroxyalkyl and fluoroalkyl, or $R^4$ and $R^5$ taken together represent double-bonded oxygen, R6 and R7 taken together form a carbon-carbon double bond, $R^8$ may be H or $CH_3$, and wherein n is an integer having a value of from 1 to 5, and wherein the carbon at any one of positions 20, 22, or 23 in the side chain may be replaced by an O, S, or N atom.

One would also preferably wish to use the compounds found in U.S. patent application Ser. No. 10/997,698 (incorporated by reference), Vitamin D Analogs For Obesity Prevention and Treatment, which describes various useful 1α-dihydroxyvitamin $D_3$ and vitamin $D_2$ compounds along with particularly advantageous 19-nor compounds. By "19-nor compounds" we mean the general formulas presented in Ser. No. 10/997,698 and Appendix A.

Additionally, one would also use HECTOROL® (Bone Care International, Inc.; Madison, Wis.), which is disclosed in U.S. Pat. Nos. 4,195,027; 4,202,829; 4,260,549; 4,554,106; and 4,555,364, each of which is incorporated herein by reference as if set forth in its entirety. Furthermore, one would use compounds such as CALDEROL™ (Organon, Inc.; Roseland, N.J.) ONE-ALPHA™ (Leo Pharmaceutical Products, LTD; Ballerup, Denmark), ALPHA D3™ (Teva Pharmaceuticals Industries, LTD; Petach Tikva, Israel), ONEALFA™ (Teijin Pharmaceuticals, LTD; Tokyo, Japan), ALFAROL™ (Chugia Pharmaceutical Co., LTD; Tokyo, Japan), ROCALTROL® (Hoffman-La Roche Pharmaceutical, Inc.; Nutley, N.J.), ZEMPLAR® (Abbott Laboratories; Abbott Park, Ill.), CALCIJEX® (Abbott Laboratories; Abbott Park, Ill.), DOVONEX® (Leo Pharmaceutical Products, LTD; Ballerup, Denmark) or TACALCITOL™ (Teijin Pharmaceuticals, LTD; Tokyo, Japan), all of which are drug forms of 1α-dihydroxyvitamin $D_3$. Likewise, Prosser D & Jones G, "Vitamin D analogs," Curr. Med. Chem.—Imm., Endooc. & Metab. Agents 1:217-234 (2001), discloses useful vitamin D analogs. Finally, one would also use the compounds described in U.S. patent application Ser. No. 10/405,653 or U.S. Pat. No. 5,716,946, each of which is incorporated herein by reference as if set forth in its entirety.

One may also wish to use fluorovitamin D compounds, such as those described in the following U.S. Pat. Nos.: 4,188,345; 4,196,133; 4,201,881; 4,224,230; 4,226,787; 4,226,788; 4,229,357; 4,229,358; 4,230,627; 4,248,791; 4,254,045; 4,263,214; 4,305,880; 4,307,025; 4,358,406; 4,441,833; 4,500,460; 4,502,991; 4,552,698; 4,564,474; 4,594,192; each of which is incorporated herein by reference as if set forth in its entirety.

We envision that the combination of calcitonin and vitamin D will be effective to reduce or eliminate MS symptoms. An advantage of combining both vitamin D and calcitonin would be improved effectiveness without danger of hypercalcemia. These two agents should be synergistic because they function by different mechanisms and at different sites.

One would preferably administer vitamin D in the following manner: The vitamin D compound may be administered orally in pills, capsules, and liquids. Vitamin D compounds can also be administered by injection in a suitable solvent or carrier as is Calcijex, Hectorol or Zemplar. It may also be given by nasal or pulmonary routes. A medication may also be envisioned whereby calcitonin and vitamin D compounds are provided in the same formulation, as for example in a solvent suitable for nasal application or by inhalation as an aerosol.

Most preferably, one would dose the animal with the vitamin D compound at the concentrations described in the citations above and below (see U.S. Pat. No. 5,716,946, incorporated by reference).

The above compounds exhibit a desired, and highly advantageous, pattern of biological activity. Generally, the amount of vitamin D analog administered to the subject ranges from about 0.01 μg to about 100 mg per day and in some embodiments ranges from about 0.1 μg to about 1000 μg per day. In some such embodiments, the analogs are present in a pharmaceutical formulation or medicament that includes a carrier. In some such embodiments, the amount of compound administered to the subject ranges from about 0.01 μg to about 100 mg per day and in other embodiments ranges from about 0.1 μg to about 1000 μg per day and in other embodiments ranges from 0.1 μg to about 50 μg per day. In some compositions, the amount of the vitamin D analog in the composition ranges from about 0.01 μg/gram to about 1000 μg/gram, and in some such embodiments the amount of analog in the composition ranges from about 0.1 μg/gram to about 50 μg/gram. It will be understood that the dosage will be based on numerous factors set forth herein and on the specific activity of the given compound.

In another embodiment, the present invention is a composition comprising both calcitonin and 1,25-dihydroxyvitamin D analog. This medication would preferably be at a dosage described above for calcitonin and vitamin D analogs at or below that described in the citation above and is preferably in a formulation suitable for IV, nasal or aerosol administration. One may wish to add pharmaceutical carriers known to those of skill in the art.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims herein for interpreting the scope of the invention.

EXAMPLES

Example 1

To determine the effect of calcitonin on the murine model of MS, experimental autoimmune encephalomyelitis (EAE), 25-hydroxyvitamin $D_3$-1α-hydroxylase knockout mice (1α-OH KO) were maintained on a purified diet containing 0.87% calcium and 1 ng 1,25-$(OH)_2D_3$ (Vit D) for two to three weeks prior to EAE immunization. EAE was induced at six to ten weeks of age by subcutaneous immunization of 200 μg of the immunodominant peptide to myelin oligodendrocyte glycoproprotein ($MOG_{35-55}$).

The peptide was synthesized at University of Wisconsin Biotechnology Center using standard 9-fluorenyl-methoxycarbonyl chemistry. The peptide was dissolved in Freund's complete adjuvant (CFA; Sigma; St. Louis, Mo.) containing 4 mg/ml of heat-inactivated *Mycobacterium tuberculosis* H837a (Difco Laboratories; Detroit, Mich.).

Mice were injected with 200 ng of *Bordetella pertussis* toxin (List Biological Laboratories, Campbell, Calif.) on the day of immunization and 48 hours later. The mice were examined daily for clinical signs of EAE utilizing the following scoring system: 0, no sign; 1, limp tail; 2, hindlimb weakness; 3, hindlimb paralysis; 4, forelimb paralysis; 5, moribund or death.

Salmon calcitonin (sCT; Bachem California; Torrence, Calif.) was dissolved to a concentration of 1 mg/ml in a vehicle containing 150 mM NaCl, 1 mM HCl, and 2% heat inactivated sera. The serum used was from 1α-OH KO mice matched by sex to the group of mice receiving the treatment. SCT was chronically administered using Alzet osmotic minipumps model 1002 (Durect Corp.; Cupertino, Calif.) calibrated to deliver 0.25 μl/hour over a 15 day period.

Ten days after immunization, mice were weighed and the pumps were filled with either vehicle or sCT diluted to deliver 6 μg/kg of body weight per day to each mouse. The pumps were surgically placed subcutaneously in the upper back of mice anesthetized with 2% isofluorane. At the end of the study, successful delivery of the sCT was assessed by two methods. First, the fluid volume remaining in the pump reservoirs was measured. Second, the remaining sCT was pooled and intraperitoneally injected into 1α-knockout mice that were not included in the initial study. Serum calcium measurements were taken six hours after injection to determine if sCT maintained its bioactivity throughout the study. Blood samples were collected at multiple time-points throughout the study to monitor changes in serum calcium levels. Blood was obtained by the orbital bleed method. Approximately 150 μl was collected per mouse.

Collected blood samples were centrifuged at 6000 rpm for 15 minutes; followed by another 60-second spin at 14000 rpm. Serum samples were diluted in 0.1% $LaCl_3$ and serum calcium values were measured using a Perkin Elmer atomic absorption spectrometer.

Statistical analysis was performed using the two-tailed Fisher exact probability test on incidence rates and the unpaired Student's t-test on all other measurements. Values of $P<0.05$ were considered statistically significant.

The results of the experiment in female 1α-OH KO mice are described in FIG. 1A-1B, as well as Table 2. The results of the experiment in 1α-OH KO male mice are described in FIG. 2A-2B, as well as Table 3. As shown in FIG. 1A, serum calcium levels of female 1α-OH KO mice were generally unaffected by administration of 6 μg/kg of calcitonin. However, as shown in FIG. 1B and Table 2, sCT delayed and diminished the EAE score in female 1α-OH KO mice treated with calcitonin compared to mice treated with vehicle alone.

Figure 2:
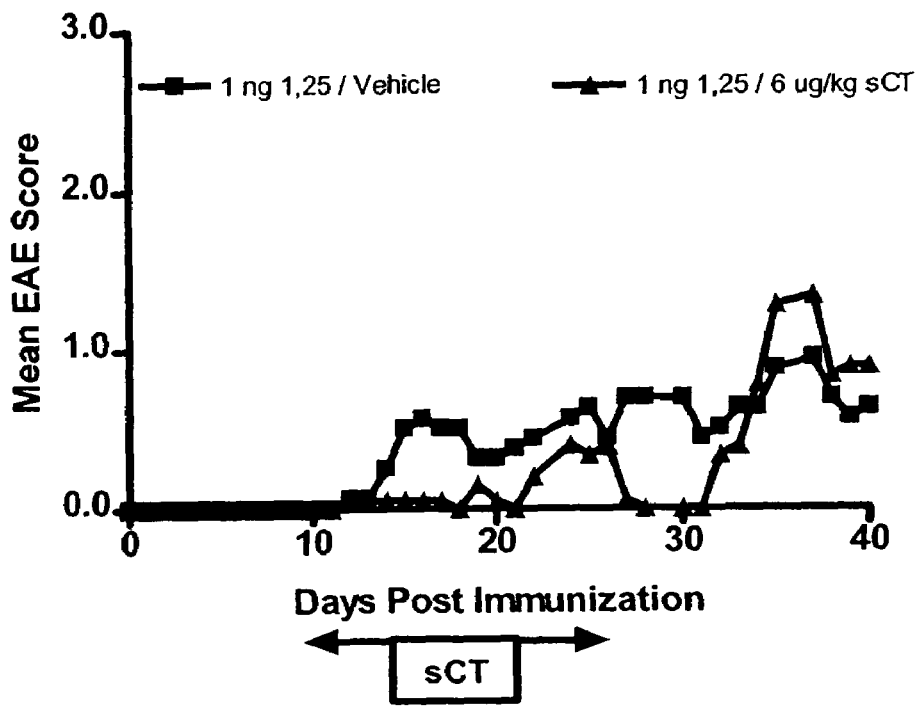
FIG. 2 is a set of graphs corresponding to those in FIG. 1 except that the mice are male in the FIG. 2 graphs.
Figure 2:
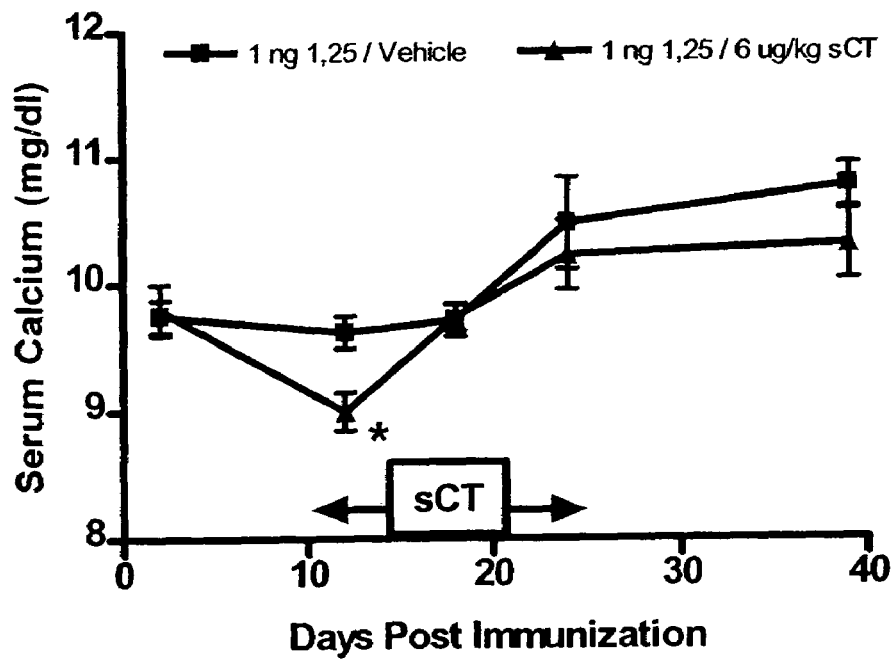

As shown in FIG. 2A, serum calcium levels of male 1α-OH KO mice were also unaffected by administration of 6 μg/kg of calcitonin. Similarly, FIG. 2B and Table 3, show that sCT lowered the EAE score in male 1α-OH KO mice treated with calcitonin compared to mice treated with vehicle alone. The male 1α-OH KO mice treated with calcitonin produced a similar, but lesser, reduction in the EAE score than female 1α-OH KO mice treated with calcitonin.

This Example demonstrates the effectiveness of sCT delivery with use of a minipump. We envision that optimization of calcitonin delivery will result in improved reduction of multiple sclerosis symptoms.

TABLE 2

Incidence and Onset of Disease in Female 1α-KO Maintained on 0.87% Calcium + 1 ng Vitamin D Diet.

|  | Vehicle | sCT |
|---|---|---|
| Incidence | 5/6 sick | 3/7 sick |
| % Sick | 83.3 | 42.9 |

TABLE 2-continued

Incidence and Onset of Disease in Female 1α-KO Maintained on
0.87% Calcium + 1 ng Vitamin D Diet.

|  | Vehicle | sCT |  |
| --- | --- | --- | --- |
| Mean Onset Day | 32 ± 3 | 41 ± 11 | P = 0.297 |
| Severity | 2.6 ± 0.9 | 1.3 ± 0.6 | P = 0.051 |

TABLE 3

Incidence and Onset of Disease in Male 1α-KO Maintained on
0.87% Calcium + 1 ng Vitamin D Diet.

|  | Vehicle | sCT |  |
| --- | --- | --- | --- |
| Incidence | 4/8 sick | 2/7 sick |  |
| % Sick | 50.0 | 28.6 |  |
| Mean Onset Day | 19 ± 5 | 30 ± 8 | P = 0.201 |
| Severity | 2.1 ± 0.6 | 2.5 ± 0.7 | P = 0.145 |

Example 2

To determine the effect of calcitonin on EAE in mice, female mice were maintained as described above. The strain of mouse used in this experiment was C57BL6 which was obtained from Harlan Labs and therefore should be designated C57BL6h. The only difference from the experiment above is that these mice were fed a regular chow diet (Formulab Chow 5008, PMI Labdiet).

EAE was induced as described above. Mice were injected with 200 ng of *B. pertussis* toxin on the day of immunization and 48 hours later.

sCT was prepared as described above. One week after immunization, mice were weighed and the pumps were filled with vehicle, 6 μg/kg of sCT per day of body weight to each mouse. The pumps were surgically placed subcutaneously in the upper back of mice anesthetized with 2% isofluorane. At the end of the study, successful delivery of the sCT was assessed by two methods. First, the fluid volume remaining in the pump reservoirs was measured. Second, the remaining sCT was pooled and intraperitoneally injected into mice that were not included in the initial study. Serum calcium measurements were taken six hours after injection to determine if sCT maintained its bioactivity throughout the study.

Mice were examined daily, for over two weeks, for clinical signs of EAE utilizing the following scoring system described above.

Blood samples were collected at multiple time-points and prepared and analyzed as described above. Likewise, statistical analysis was performed as noted above.

Figure 3:
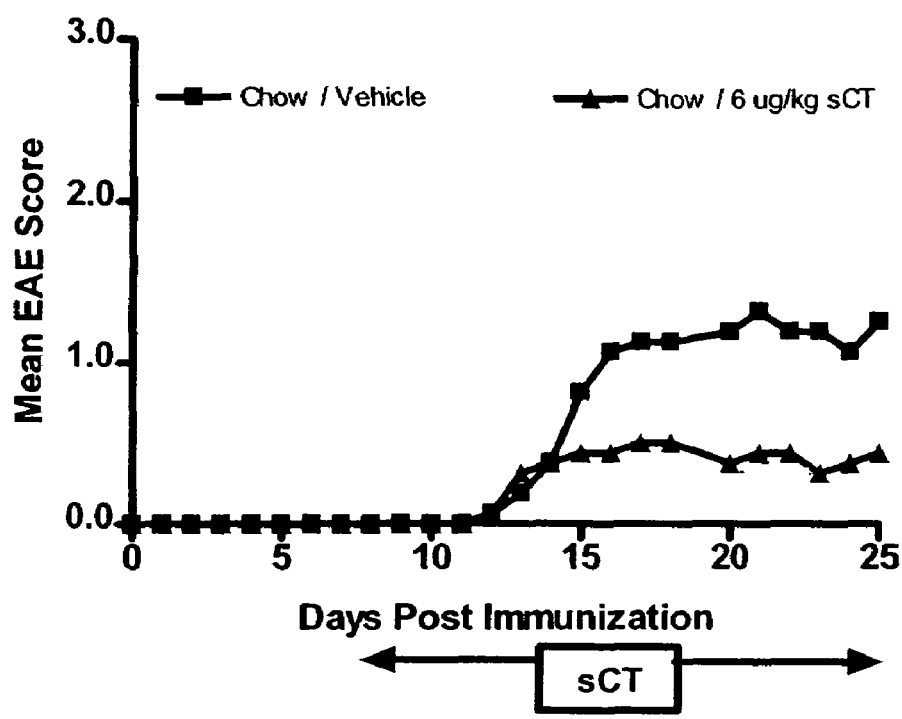
FIG. 3 diagrams mean EAE score versus days post immunization to determine the effect of calcitonin on EAE in female mice.

The results of the experiments in female B6h mice are described in FIG. 3, as well as and Table 4. As shown in FIG. 3, sCT delayed and diminished the EAE score in female C57BL6h mice treated with calcitonin compared to mice treated with vehicle alone.

TABLE 4

Incidence and Onset of Disease in Female Mice Maintained on
0.87% Calcium + 1 ng Vitamin D Diet.

|  | Vehicle | SCT |
| --- | --- | --- |
| Incidence | 5/8 sick | 2/8 sick |
| % Sick | 62.3 | 25.0 |

TABLE 4-continued

Incidence and Onset of Disease in Female Mice Maintained on
0.87% Calcium + 1 ng Vitamin D Diet.

|  | Vehicle | SCT |
| --- | --- | --- |
| Mean Onset Day | 16 ± 1 | 14 ± 1 |
| Severity | 2.2 ± 1.0 | 2.0 ± 0.7 |

Example 3

To determine the effect of calcitonin on EAE in C57BL/6J mice (C57BL6 mice from Jackson Labs), female mice were maintained on a standard chow diet prior to and following EAE immunization. The C57BL6J strain was chosen primarily because it is one of the few strains susceptible to MOG-induced EAE, and also because the 1α-KO has been back-crossed into the C57BL6J strain. The diet was changed primarily because the mice being used were wild-type and no longer required the supplemented $1,25(OH)_2D_3$ that the 1α-KO mice do. Additionally, we have typically seen higher incidence rates when animals are maintained on a regular chow diet versus the purified diet.

EAE was induced as described above. Mice were injected with 200 ng of *B. pertussis* toxin on the day of immunization and 48 hours later.

sCT was prepared as described above. One week after immunization, mice were weighed and the pumps were filled with vehicle, 6 μg/kg of sCT per day of body weight or 60 μg/kg of sCT per day of body weight to each mouse. The pumps were surgically placed subcutaneously in the upper back of mice anesthetized with 2% isofluorane. At the end of the study, successful delivery of the sCT was assessed by two methods. First, the fluid volume remaining in the pump reservoirs was measured. Second, the remaining sCT was pooled and intraperitoneally injected into C57BL/6J mice that were not included in the initial study. Serum calcium measurements were taken six hours after injection to determine if sCT maintained its bioactivity throughout the study.

Mice were examined daily, for over two weeks, for clinical signs of EAE utilizing the following scoring system as described above.

Blood samples were collected at multiple time-points and prepared and analyzed as described above. Likewise, statistical analysis was as performed as noted above.

Figure 4:
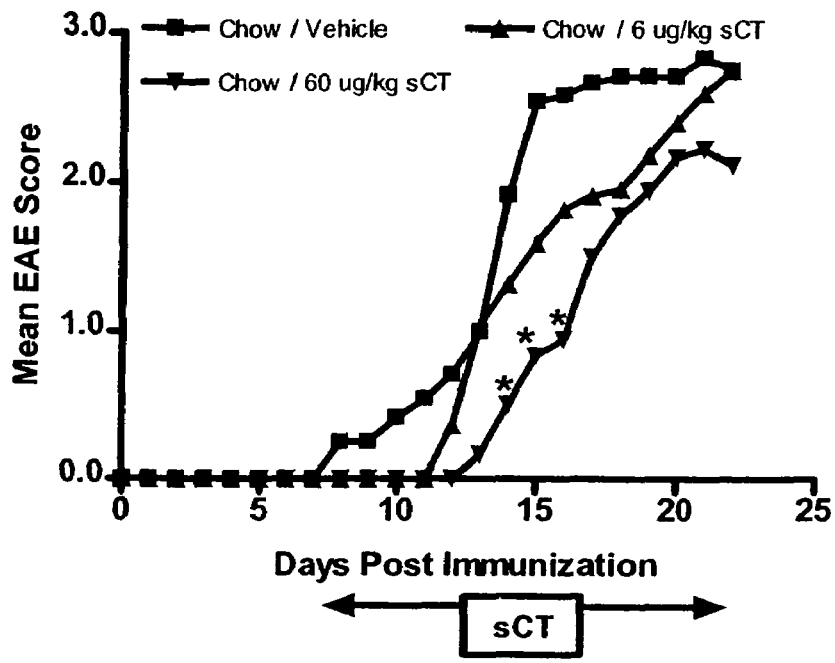
FIGS. 4A and B is a set of graphs describing (FIG. 4A) mean EAE score versus days post immunization and (FIG. 4B) serum calcium versus days post immunization for mice treated with various levels of sCT.
Figure 4:
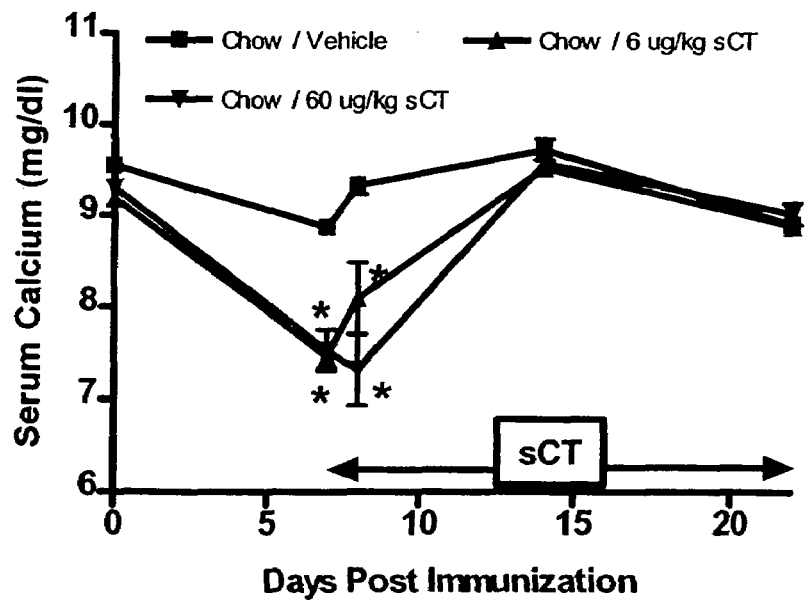

The results of the experiments in female C57BL/6J mice are described in FIG. 4A-4B, as well as Table 5. As shown in FIG. 4A, serum calcium levels of female C57BL/6J mice were initially lowered by administration of 6 μg/kg of calcitonin or 60 μg/kg of calcitonin. However, as shown in FIG. 4B and Table 5, sCT delayed and diminished the EAE score in female C57BL\6J mice administered 60 μg/kg of calcitonin compared to mice treated with vehicle alone.

Summary.

TABLE 5

Incidence and Onset of Disease in Female C57BL/6J Mice
Maintained on Standard Chow Diet.

|  | Vehicle | 6 μg/kg sCT | 60 μg/kg sCT |
| --- | --- | --- | --- |
| Incidence | 9/12 sick | 9/11 sick | 6/9 sick |
| % Sick | 75.0 | 82.0 | 67.0 |
| Mean Onset Day | 13 ± 3 | 14 ± 3 | 16 ± 2 |
| Severity | 4.2 ± 1.0 | 3.8 ± 0.6 | 3.5 ± 1.3 |

Example 4

To determine the effect of calcitonin and Vit D on EAE in C57BL/6J mice, female C57BL/6J mice were maintained on standard chow until eight weeks of age, and then switched to a purified diet containing 0.87% calcium supplemented with 1 ng or 30 ng of 1,25-$(OH)_2D_3$ for one week prior to EAE immunization.

EAE was induced as described above. Mice were injected with 200 ng of *B. pertussis* toxin on the day of immunization and 48 hours later.

sCT was prepared as described above. One week after immunization, mice were weighed and the pumps were filled with vehicle or 30 µg/kg per day of sCT of body weight to each mouse. The pumps were surgically placed subcutaneously in the upper back of mice anesthetized with 2% isofluorane. At the end of the study, successful delivery of the sCT was assessed by two methods. First, the fluid volume remaining in the pump reservoirs was measured. Second, the remaining sCT was pooled and intraperitoneally injected into C57BL/6J mice that were not included in the initial study. Serum calcium measurements were taken six hours after injection to determine if sCT maintained its bioactivity throughout the study.

Mice were examined daily, for over two weeks, for clinical signs of EAE utilizing the following scoring system as described above.

Blood samples were collected at multiple time-points and prepared and analyzed as described above. Likewise, statistical analysis was performed as noted above.

Figure 5:
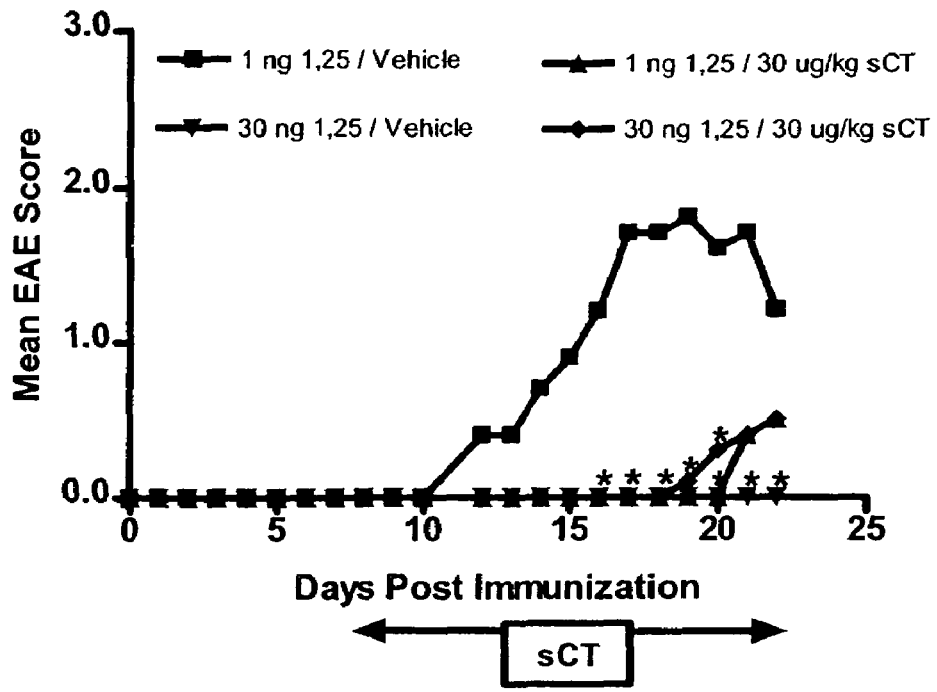
FIG. 5 is a set of graphs showing (FIG. 5A) mean EAE score versus days post immunization and (FIG. 5B) serum calcium versus days post immunization for mice treated with different levels of 1,25 $(OH)_2D_3$ and calcitonin.
Figure 5:
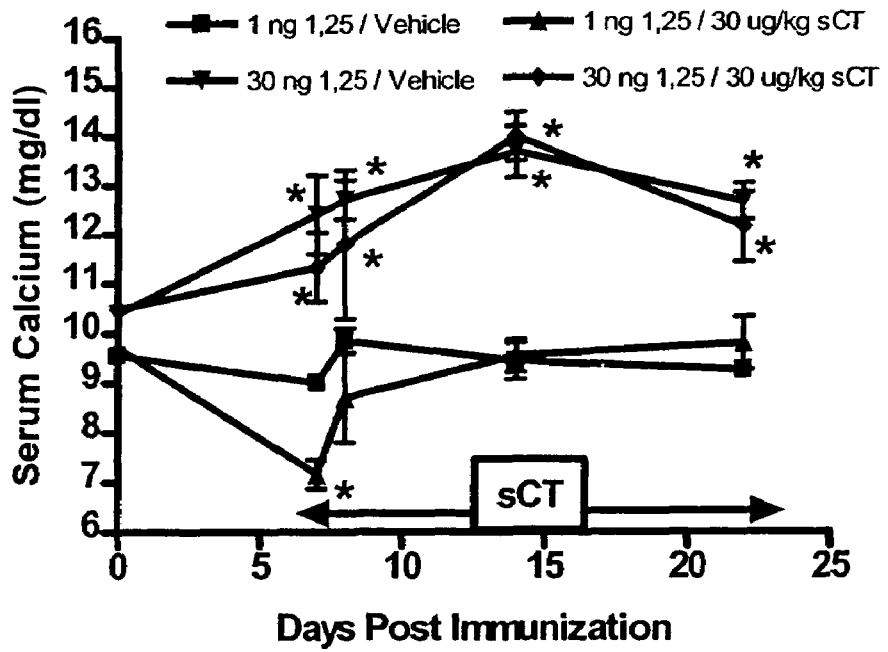

The results of the experiments in female C57BL/6J mice are described in FIG. 5A-5B and the accompanying Table 6. As shown in FIG. 5A, serum calcium levels of female C57BL/6J mice were elevated by administration of 30 ng Vit D (regardless of whether sCT was provideded) compared to female C57BL/6J mice administered 1 ng Vit D (regardless of whether sCT was provided). However, as shown in FIG. 5B and Table 6, sCT and 30 ng Vit D delayed and diminished the EAE score in female C57BL\6J mice compared to mice treated with 1 ng Vit D alone. The 1 ng 1,25+sCT group shows decreased incidence, severity, and onset compared to the 1 ng 1,25 group and equal to the 30 ng 1,25+sCT group but without the hypercalcemia.

Summary.

TABLE 6

Incidence and Onset of Disease in Female C57BL/6J Maintained on 0.87% Calcium and Different Concentrations of Vitamin D Diet.

|  | 1 ng Vit D | 1 ng Vit D + 30 µg/kg sCT | 30 ng Vit D | 30 ng Vit D + 30 µg/kg sCT |
|---|---|---|---|---|
| Incidence | 6/9 sick | 1/4 sick | 0/8 sick | 1/4 sick |
| % Sick | 67.0 | 25.0 | 0.0 | 25.0 |
| Mean Onset Day | 15 ± 2 | 21 | — | 20 |
| Severity | 2.9 ± 0.9 | 2.0 | — | 2.0 |

Example 5

To determine the effect of calcitonin in C57BL/6J mice on EAE prior to immuninization, female mice were maintained on a standard chow diet prior to and following EAE immunization.

EAE was induced as described above. Mice were injected with 200 ng of *B. pertussis* toxin on the day of immunization and 48 hours later.

sCT was prepared as described above. However, two days prior to immunization, mice were weighed and the pumps were filled with vehicle or 6 µg/kg per day of sCT of body weight to each mouse. The pumps were surgically placed subcutaneously in the upper back of mice anesthetized with 2% isofluorane. At the end of the study, successful delivery of the sCT was assessed by two methods. First, the fluid volume remaining in the pump reservoirs was measured. Second, the remaining sCT was pooled and intraperitoneally injected into C57BL/6J mice that were not included in the initial study. Serum calcium measurements were taken six hours after injection to determine if sCT maintained its bioactivity throughout the study.

Mice were examined daily, for over two weeks, for clinical signs of EAE utilizing the scoring system described above.

Blood samples were collected at multiple time-points and prepared and analyzed as described above. Likewise, statistical analysis was performed as noted above.

Figure 6:
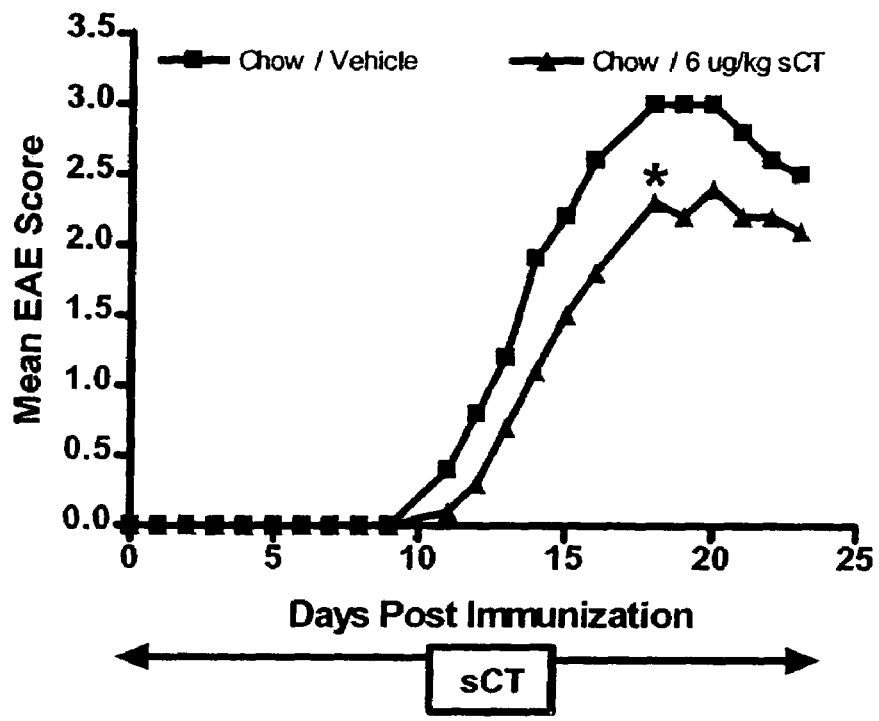
FIG. 6 is a graph describing the effect of 6 μg/kg calcitonin in female C57BL/6J mice.

The results of the experiments in female C57BL/6J mice are described in FIG. 6, as well as Table 7. As shown in FIG. 6, sCT delayed and diminished the EAE score in female C57BL\6J mice administered 6 µg/kg of calcitonin compared to mice treated with vehicle alone.

TABLE 7

Incidence and Onset of Disease in Female C57Bl/6J Mice Standard Chow Diet.

|  | Vehicle | SCT |
|---|---|---|
| Incidence | 17/18 sick | 19/20 sick |
| % Sick | 94.4 | 95.0 |
| Mean Onset Day | 13 ± 5 | 15 ± 2 |
| Severity | 3.6 ± 1.0 | 2.9 ± 1.1 |

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set for by the appended claims.

APPENDIX A

In one aspect, the invention provides methods for preventing and treating multiple sclerosis with a combination of calcitonin and a vitamin D analog in which at least one analog of 1α,25-dihydroxyvitamin $D_3$ and 1α,25-dihydroxyvitamin $D_2$ or a pharmaceutical composition that includes such an analog is administered in an effective amount to a subject, such as a multiple sclerosis subject, in need thereof. In some embodiments, the analog is a 19-nor vitamin D compound. In some such embodiments, the 19-nor vitamin D analog is modified at the 2 position. In some such embodiments, the 19-nor vitamin D analog is a 2-alkylidene 19-nor vitamin D analog such as a 2-methylene 19-nor vitamin D analog. In some embodiments, the 19-nor vitamin D analog is a (20S) 19-nor vitamin D analog such as a (20S) 2-methylene 19-nor vitamin D analog whereas in other embodiments, the 19-nor vitamin D analog is a (20R) 19-nor vitamin D analog such as a (20R) 2-methylene 19-nor vitamin D analog. In some embodiments, the analog is a compound other than (20S)-2-methylene-19-nor-1α,25-dihydroxyvitamin $D_3$ (2-MD). In some embodiments, the analog is a 2-alkyl 19-nor vitamin D analog. In some such embodiments, the analog is a 2α-alkyl 19-nor vitamin D analog such as a 2α-methyl 19-nor vitamin D analog. In other embodiments, the analog is an 18,19-dinor vitamin D analog. In some such embodiments, the analog is a 2-alkylidene 18,19-dinor vitamin D analog such as a 2-methylene 18,19-dinor vitamin D analog. In other embodiments, the analog is a 2-alkyl 18,19-dinor vitamin D analog. In some such embodiments, the analog is a 2α-alkyl 18,19-dinor vitamin D analog such as a 2α-methyl 18,19-nor vitamin D analog.

In another aspect, the invention provides methods for treating multiple sclerosis in which at least one analog of 1α,25-dihydroxyvitamin $D_3$ or 1α,25-dihydroxyvitamin $D_2$ or a pharmaceutical composition that includes such an analog is administered in an effective amount to a subject, such as a multiple sclerosis subject, in need thereof. In some embodiments, the at least one analog is a 19-nor vitamin D compound. In some such embodiments, the 19-nor vitamin D analog is modified at the 2 position. In some such embodiments, the 19-nor vitamin D analog is a 2-alkylidene 19-nor vitamin D analog such as a 2-methylene 19-nor vitamin D analog. In some embodiments, the 19-nor vitamin D analog is a (20S) 19-nor vitamin D analog such as a (20S) 2-methylene 19-nor vitamin D analog whereas in other embodiments, the 19-nor vitamin D analog is a (20R) 19-nor vitamin D analog such as a (20R) 2-methylene 19-nor vitamin D analog. In some embodiments, the analog is a compound other than (20S)-2-methylene-19-nor-1α,25-dihydroxyvitamin $D_3$ (2-MD). In some embodiments, the analog is a 2-alkyl 19-nor vitamin D analog. In some such embodiments, the analog is a 2α-alkyl 19-nor vitamin D analog such as a 2α-methyl 19-nor vitamin D analog. In other embodiments, the analog is an 18,19-dinor vitamin D analog. In some such embodiments, the analog is a 2-alkylidene 18,19-dinor vitamin D analog such as a 2-methylene 18,19-dinor vitamin D analog. In other embodiments, the analog is a 2-alkyl 18,19-dinor vitamin D analog. In some such embodiments, the analog is a 2α-alkyl 18,19-dinor vitamin D analog such as a 2α-methyl 18,19-nor vitamin D analog.

In some embodiments, the animal subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the animal subject is a primate such as, in some embodiments, a human.

In some embodiments, the 19-nor vitamin D analog administered to the subject or used to prepare a pharmaceutical formulation is a compound of formula IA or IB, or is a mixture thereof. In some such embodiments, the analog is a compound of formula IA. In other embodiments, the vitamin D analog is a compound of formula IB.

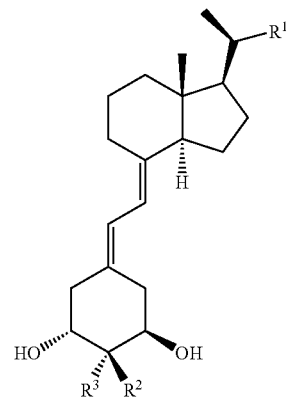

IA

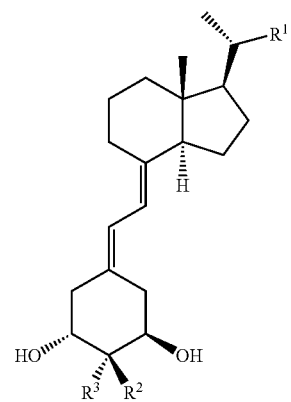

IB

In compounds of formula IA and IB, $R^1$ is selected from H, or straight or branched chain alkyl groups having from 1 to 8 carbon atoms, straight or branched chain alkenyl groups having from 2 to 8 carbon atoms, straight or branched chain □ydroxyl-substituted alkyl groups having from 1 to 8 carbon atoms, or straight and branched chain □ydroxyl-substituted alkenyl groups having from 2 to 8 carbon atoms. In some such embodiments, $R^1$ is selected from straight or branched chain alkyl groups having from 2 to 7 carbon atoms, straight or branched chain alkenyl groups having from 2 to 7 carbon atoms, straight or branched chain □ydroxyl-substituted alkyl groups having from 2 to 6 carbon atoms, or straight or branched chain □ydroxyl-substituted alkenyl groups having from 2 to 6 carbon atoms. In other such embodiments, $R^1$ is selected from straight or branched chain alkyl groups having from 2 to 7 carbon atoms, straight or branched chain alkenyl groups having from 2 to 7 carbon atoms, or straight or branched chain □ydroxyl-substituted alkenyl groups having from 2 to 6 carbon atoms.

In compounds of formula IA and IB, $R^2$ and $R^3$ are independently selected from H, straight or branched chain alkyl groups having from 1 to 8 carbon atoms, or straight or branched chain alkenyl groups having from 1 to 8 carbon atoms or $R^2$ and $R^3$ join together to form a group of formula IC

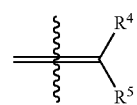

IC where the wavy line indicates the point of attachment to the carbon at the 2 position of the vitamin D analog and $R^4$ and $R^5$ are independently selected from H, straight or branched chain alkyl groups having from 1 to 8 carbon atoms, straight or branched chain hydroxyalkyl groups having from 1 to 8 carbon atoms, straight or branched chain hydroxyalkenyl groups having from 1 to 8 carbon atoms, straight or branched chain protected hydroxyalkyl groups having from 1 to 8 carbon atoms, straight or branched chain fluoroalkyl groups having from 1 to 8 carbon atoms, or straight or branched chain alkenyl groups having from 1 to 8 carbon atoms. In some embodiments, the analog is a compound of formula IA or IB and $R^3$ is H. In some such embodiments, $R^2$ is a straight chain alkyl group such as methyl, ethyl, or propyl. In other embodiments, $R^2$ and R join together to form a group of formula IC in which $R^4$ and $R^5$ are both H. Examples of some such compounds include compounds of formula IIA and IIB.

In some embodiments, the 19-nor vitamin D analog administered to the subject or used to prepare a pharmaceutical formulation is a compound of formula IIA or IIB, or is a mixture thereof. In some such embodiments, the vitamin D analog is a compound of formula IIA. In other embodiments, the vitamin D analog is a compound of formula IIB.

selected from straight or branched chain alkyl groups having from 2 to 7 carbon atoms, straight or branched chain alkenyl groups having from 2 to 7 carbon atoms, straight or branched chain hydroxyl-substituted alkyl groups having from 2 to 6 carbon atoms, or straight or branched chain hydroxyl-substituted alkenyl groups having from 2 to 6 carbon atoms. In other such embodiments, $R^1$ is selected from straight or branched chain alkyl groups having from 2 to 7 carbon atoms, straight or branched chain alkenyl groups having from 2 to 7 carbon atoms, or straight or branched chain hydroxyl-substituted alkenyl groups having from 2 to 6 carbon atoms. In some embodiments, the compound is a compound of formula IIA or IIB other than (20S)-2-methylene-19-nor-1α,25-dihydroxyvitamin $D_3$ (2-MD) or a compound of formula IIC.

In some embodiments, the compound of formula IA, IB, IIA, or IIB is a compound of formula IA, IB, IIA, or IIB where $R^1$ is selected from one of the following groups where the wavy line over a straight bond indicates the point of attachment to the rest of the molecule and a wavy line originating at a carbon indicates that both or either of the S or R configurations is contemplated at that position.

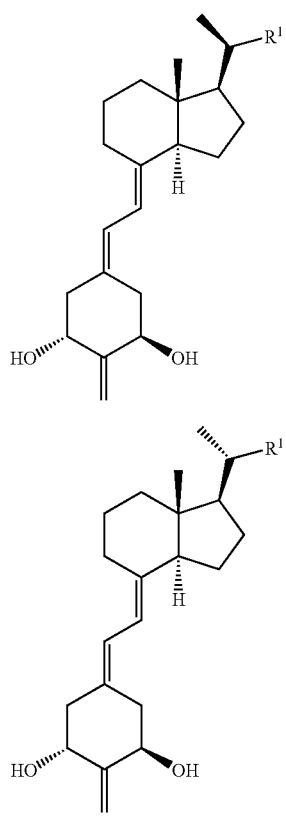

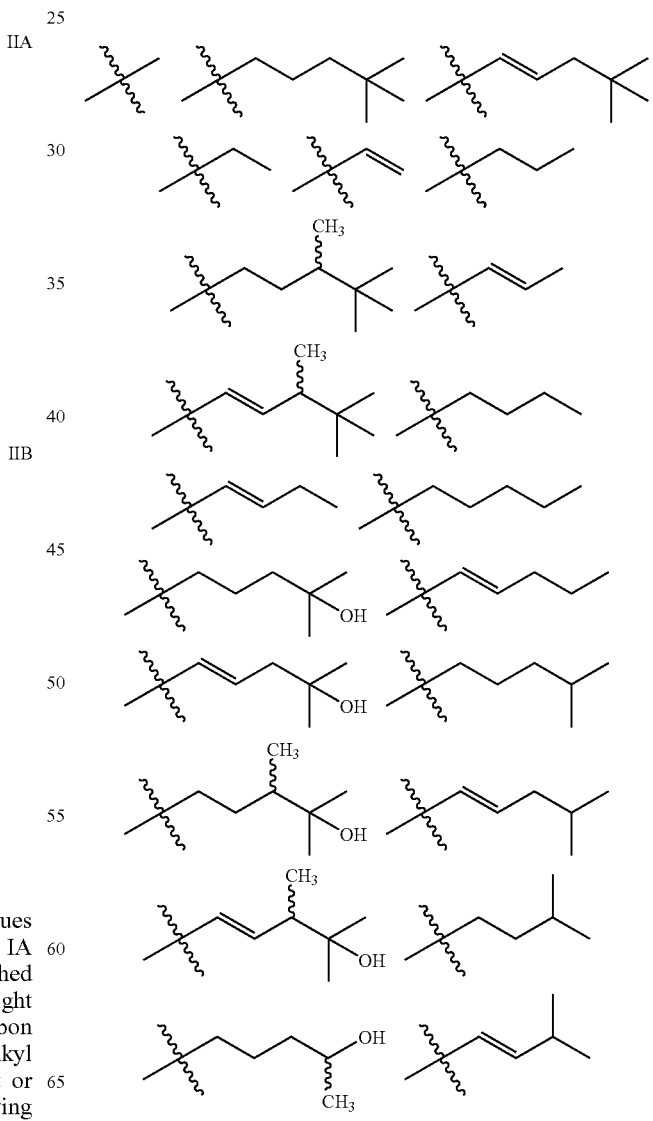

In compounds of formula IIA and IIB, $R^1$ has the same values as set forth above with respect to compounds of formula IA and IB. Thus, $R^1$ is selected from H, or straight or branched chain alkyl groups having from 1 to 8 carbon atoms, straight or branched chain alkenyl groups having from 2 to 8 carbon atoms, straight or branched chain hydroxyl-substituted alkyl groups having from 1 to 8 carbon atoms, or straight or branched chain hydroxyl-substituted alkenyl groups having from 2 to 8 carbon atoms. In some such embodiments, $R^1$ is

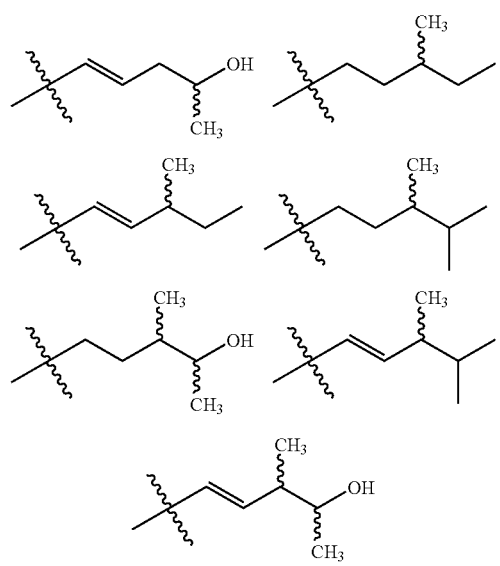

For the alkenyl groups shown above, it will be understood that with respect to the structures shown above, both the cis and trans (Z and E) isomers and mixtures thereof are contemplated.

In some embodiments, the 19-nor vitamin D analog administered to the subject or used to prepare a pharmaceutical formulation is a compound of formula IIC where $R^1$ is a □ydroxyl-substituted branched chain alkyl group having 6 carbon atoms (a —$CH_2CH_2CH_2C(CH_3)_2OH$ group), and the compound has the name (20S)-2-methylene-19-nor-1α,25-dihydroxyvitamin $D_3$ (2-MD).

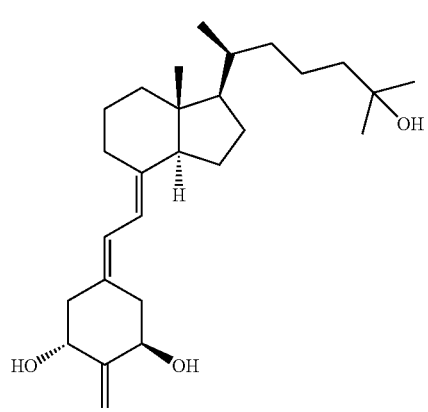

IIC

In some embodiments, the 19-nor vitamin D analog administered to the subject or used to prepare a pharmaceutical formulation is a compound of formula IID where $R^1$ is a branched chain alkyl group having 7 carbon atoms (a —$CH_2CH_2CH_2C(CH_3)_3$ group), and the compound has the name (20S)-1α-hydroxy-2-methylene-19-nor-25-methylvitamin $D_3$ (TMM).

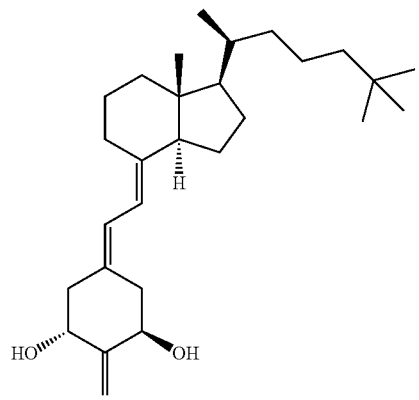

IID

In some embodiments, the 19-nor vitamin D analog administered to the subject or used to prepare a pharmaceutical formulation is a compound of formula IIE where $R^1$ is a straight chain alkyl group having 2 carbon atoms (a —$CH_2CH_3$ group), and the compound has the name (20S)-1α-hydroxy-2-methylene-19-nor-bishomopregnacalciferol (2-MbisP).

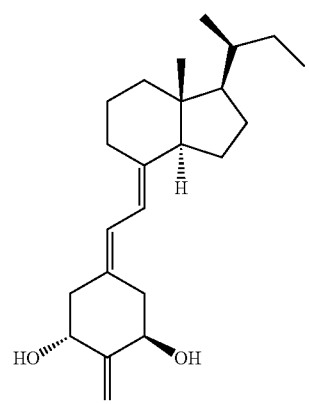

IIE

In some embodiments, the 19-nor vitamin D analog administered to the subject or used to prepare a pharmaceutical formulation is a compound of formula IIF where $R^1$ is a straight chain alkyl group having 1 carbon atom (a —$CH_3$ group), and the compound has the name 1α-hydroxy-2-methylene-19-nor-homopregnacalciferol (2-MP).

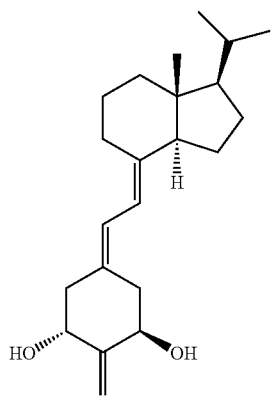

IIF

In some embodiments, the 19-nor vitamin D analog administered to the subject or used to prepare a pharmaceutical formulation is a compound of formula IIG where $R^1$ is a straight chain alkyl group having 2 carbon atoms (a —CH$_2$CH$_3$ group), and the compound has the name (20R)-1α-hydroxy-2-methylene-19-nor-bishomopregnacalciferol ((20R)2MbisP).

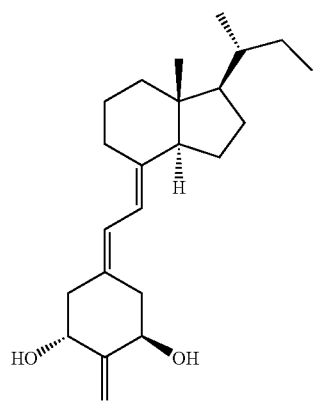

IIG

In some embodiments, the 19-nor vitamin D analog administered to the subject or used to prepare a pharmaceutical formulation is a compound of formula IIH where $R^1$ is a H, and the compound has the name 2-methylene-19-nor-1α-hydroxy-pregnacalciferol (2-Mpregna).

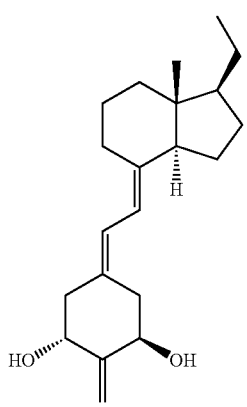

IIH

In some embodiments, the 19-nor vitamin D analog administered to the subject or used to prepare a pharmaceutical formulation is a compound of formula IIJ where $R^1$ is a straight chain alkyl group having 2 carbon atoms (a —CH$_2$CH$_3$ group), $R^2$ is a methyl group, and $R^3$ is H, and the compound has the name 2α-methyl-19-nor-(20S)-1α-hydroxy-bishomopregnacalciferol ((20S)2αMbisP).

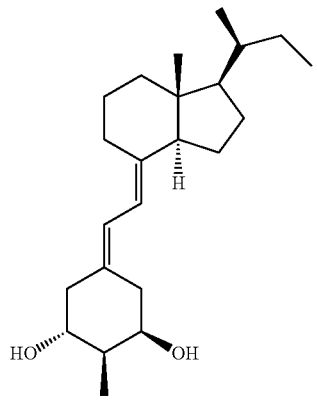

IIJ

In some embodiments, the 19-nor vitamin D analog administered to the subject or used to prepare a pharmaceutical formulation is a compound of formula IIK where $R^1$ is a straight chain alkyl group having 1 carbon atoms (a —CH$_3$ group), $R^2$ is a methyl group, and $R^3$ is H, and the compound has the name 2α-methyl-19-nor-1α-hydroxy-homopregnacalciferol (2α-methyl MP).

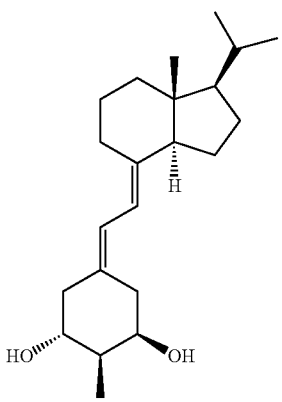

IIK

In some embodiments, the 19-nor vitamin D analog administered to the subject or used to prepare a pharmaceutical formulation is a compound of formula IIL where $R^1$ is a straight chain alkyl group having 3 carbon atoms (a —CH$_2$CH$_2$CH$_3$ group), and the compound has the name 2-methylene-19-nor-(20S)-1α-hydroxy-trishomopregnacalciferol (2MtrisP).

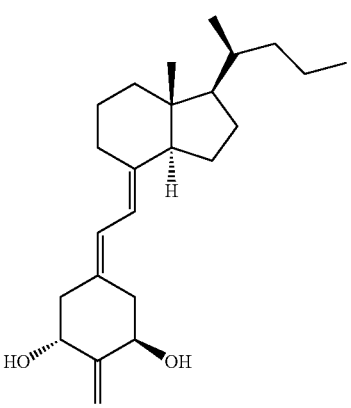

IIL

In some embodiments, the 19-nor vitamin D analog administered to the subject or used to prepare a pharmaceutical formulation is a compound of formula IIM where $R^1$ is a straight chain alkyl group having 4 carbon atoms (a —$CH_2CH_2CH_2CH_3$ group), and the compound has the name 2-methylene-19,26,27-trinor-(20S)-1α-hydroxyvitamin $D_3$ ((20S)OM).

IIM

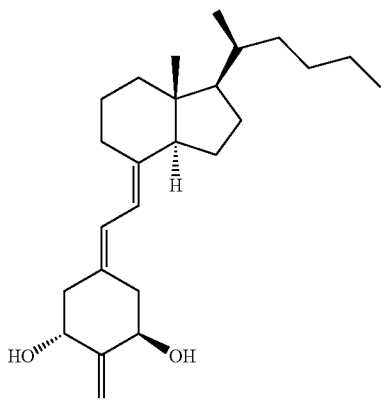

In some embodiments, the 19-nor vitamin D analog administered to the subject or used to prepare a pharmaceutical formulation is a compound of formula IIN where $R^1$ is a straight chain alkyl group having 4 carbon atoms (a —$CH_2CH_2CH_2CH_3$ group), $R^2$ is a methyl group, $R^3$ is H, and the compound has the name 2α-methyl-19,26,27-trinor-(20S)-1α-hydroxyvitamin $D_3$ (2α-methyl-19,26,27-trinor).

IIN

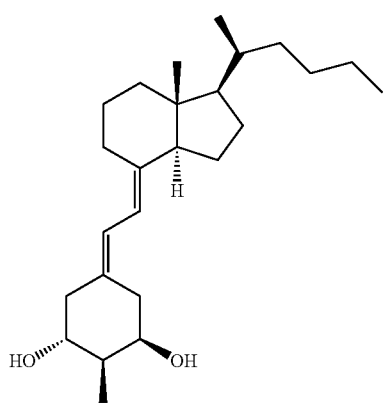

In some embodiments, the 19-nor vitamin D analog administered to the subject or used to prepare a pharmaceutical formulation is a compound of formula IIO where $R^1$ is a ☐ydroxyl-substituted branched chain alkyl group having 6 carbon atoms (a —$CH_2CH_2CH_2C(CH_3)_2OH$ group), $R^2$ and $R^3$ are a group of formula IC, $R^4$ is H, $R^5$ is a hydroxypropyl group, and the compound has the name 2-(3'-hydroxypropylidene)-19-nor-(20S)-1α,25-dihydroxyvitamin $D_3$ (1AGS).

IIO

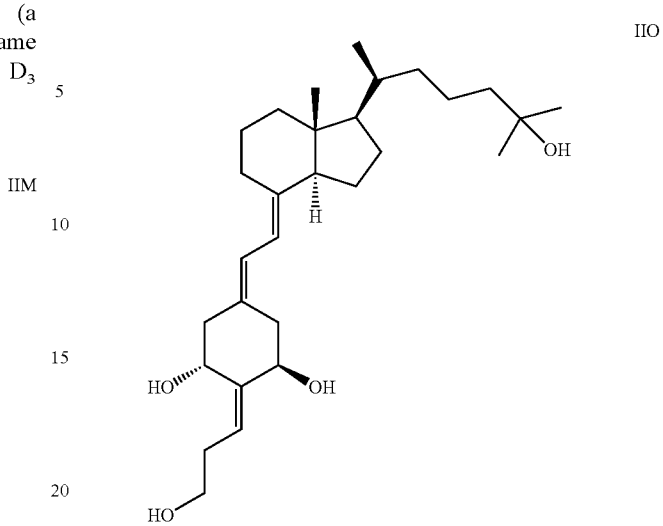

In some embodiments, the 19-nor vitamin D analog administered to the subject or used to prepare a pharmaceutical formulation is a compound of formula IIP where $R^1$ is a ☐ydroxyl-substituted branched chain alkyl group having 6 carbon atoms (a —$CH_2CH_2CH_2C(CH_3)_2OH$ group), $R^2$ and $R^3$ are a group of formula IC, $R^4$ is H, $R^5$ is a hydroxypropyl group, and the compound has the name 2-(3'-hydroxypropylidene)-19-nor-1α,25-dihydroxyvitamin $D_3$ (1AGR).

IIP

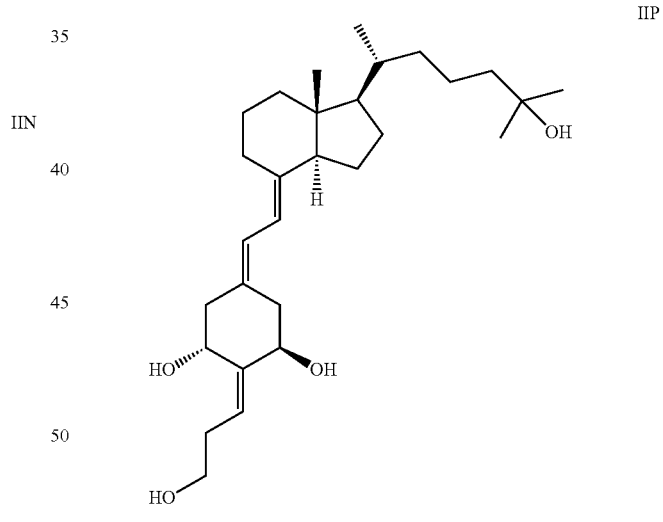

In some embodiments, the 19-nor vitamin D analog administered to the subject or used to prepare a pharmaceutical formulation is a compound of formula IIQ where $R^1$ is a ☐ydroxyl-substituted branched chain alkyl group having 6 carbon atoms (a —$CH_2CH_2CH_2C(CH_3)_2OH$ group), $R^2$ and $R^3$ are a group of formula IC, $R^4$ is H, $R^5$ is a —$CH_2CH_2OCH_2OCH_3$ group (a protected hydroxyalkyl group), and the compound has the name 2-[(3'-methoxymethoxy)-propylidene]-19-nor-1α,25-dihydroxyvitamin $D_3$ (F-Wit).

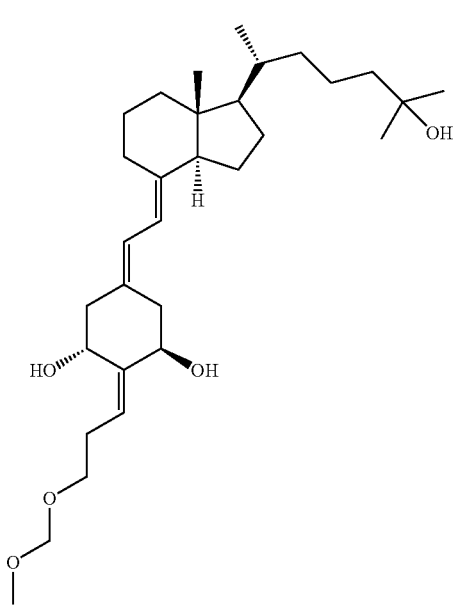

IIQ

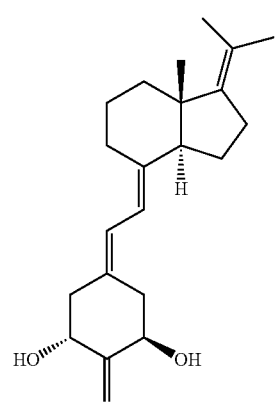

IIS

In some embodiments, the 19-nor vitamin D analog administered to the subject or used to prepare a pharmaceutical formulation is a 19,21-dinor vitamin $D_3$ analog or is a 19,21-dinor vitamin $D_2$ analog having the name 2-methylene-19,21-dinor-1α-hydroxybishomopregnacalciferol (19,21-dinor) and having the formula IIR.

In some embodiments, the 19-nor vitamin D analog administered to the subject or used to prepare a pharmaceutical formulation is an 18,19-dinor vitamin $D_3$ analog or is an 18,19-dinor vitamin $D_2$ analog. In some such embodiments, the compound has the name 2-methylene-18,19-dinor-(20S)-1α,25-dihydroxyvitamin $D_3$ (VD-03) and has the formula IIT. In other such embodiments, the compound has the name 2-methylene-18,19-dinor-1α-hydroxyhomopregnacalciferol (18,19-dinor-2MP) and has the formula IIU.

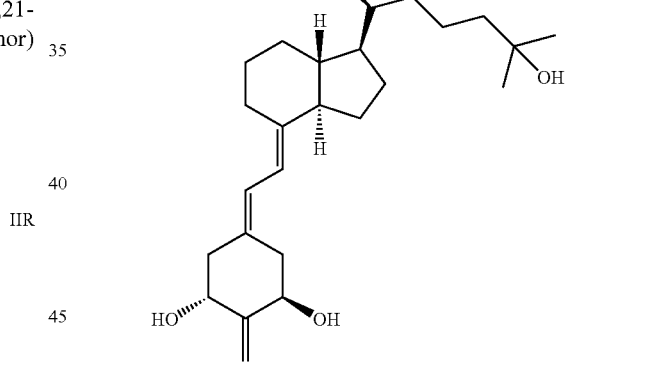

IIR / IIT

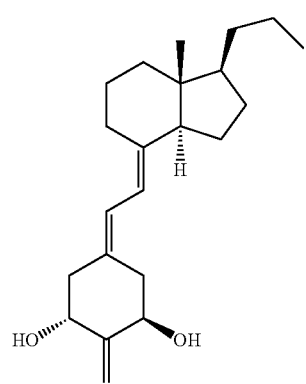

In some embodiments, the 19-nor vitamin D analog administered to the subject or used to prepare a pharmaceutical formulation is a 19-nor 17-ene vitamin $D_3$ analog or is a 19-nor 17-ene vitamin $D_2$ analog having the name 2-methylene-19-nor-1α-hydroxy-17-ene-homopregnacalciferol (Vitamin I or VIT-I) and having the formula IIS.

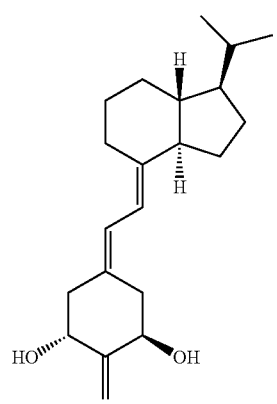

IIU

In some embodiments, the compound administered to the subject or used to prepare a pharmaceutical formulation is a 19-nor vitamin $D_2$ analog. In some such embodiments, the compound has the name 2-methylene-19-nor-24-epi-1α,25-dihydroxyvitamin $D_2$ ((24epi)$D_2$) and has the formula IIV. In other such embodiments, the compound has the name 19-nor-1α,25-dihydroxyvitamin $D_2$ (1α,25(OH)$_2$(19nor)$D_2$ or Zemplar) and has the formula IIW.

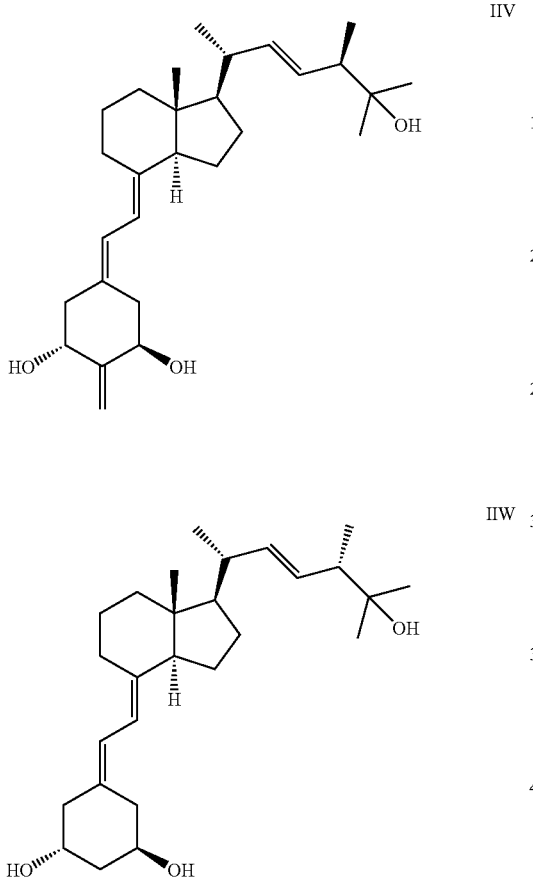

In various embodiments, the 19-nor vitamin D analog is administered orally, parenterally, transdermally, or topically. In some such embodiments, the 19-nor vitamin D analog is administered orally. In other embodiments, the 19-nor vitamin D analog is administered by injection or via suppository. In other embodiments, the 19-nor vitamin D analog is administered intravaginally.

The above compounds exhibit a desired, and highly advantageous, pattern of biological activity. Generally, the amount of vitamin D analog administered to the subject ranges from about 0.001 μg to about 100 mg per day and in some embodiments ranges from about 0.1 μg to about 1000 μg per day. In some such embodiments, the analogs are present in a pharmaceutical formulation or medicament that includes a carrier. In some such embodiments, the amount of compound administered to the subject ranges from about 0.001 μg to about 100 mg per day and in other embodiments ranges from about 0.1 μg to about 1000 μg per day and in other embodiments ranges from 0.1 μg to about 50 μg per day. In some compositions, the amount of the vitamin D analog in the composition ranges from about 0.01 μg/gram to about 1000 μg/gram, and in some such embodiments the amount of analog in the composition ranges from about 0.1 μg/gram to about 50 μg/gram. It will be understood that the dosage will be based on numerous factors set forth herein and on the specific activity of the given compound.

---

We claim:

1. A pharmaceutical preparation comprising salmon calcitonin (sCT) combined with a 1,25-dihydroxyvitamin D analog in an amount effective to relieve multiple sclerosis symptoms.

2. The preparation of claim 1 combined with a pharmaceutically acceptable carrier.

3. The preparation of claim 1 comprising 1-1000 IU salmon calcitonin and 0.01 μg-1000 μg vitamin D analog.

4. The preparation of claim 1 comprising 0.1 μg-100 μg vitamin D analog and 50-500 IU salmon calcitonin.

* * * * *

SEQUENCE LISTING

<160> NUMBER OF SEQ ID NOS: 6

<210> SEQ ID NO 1
<211> LENGTH: 32
<212> TYPE: PRT
<213> ORGANISM: Bovine

<400> SEQUENCE: 1

Cys Ser Asn Leu Ser Thr Cys Val Leu Ser Ala Tyr Trp Lys Asp Leu
1               5                   10                  15

Asn Asn Tyr His Arg Phe Ser Gly Met Gly Phe Gly Pro Glu Thr Pro
            20                  25                  30

<210> SEQ ID NO 2
<211> LENGTH: 32
<212> TYPE: PRT

```
-continued

<213> ORGANISM: Eel

<400> SEQUENCE: 2

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 3
<211> LENGTH: 32
<212> TYPE: PRT
<213> ORGANISM: Human

<400> SEQUENCE: 3

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 4
<211> LENGTH: 32
<212> TYPE: PRT
<213> ORGANISM: Porcine

<400> SEQUENCE: 4

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

<210> SEQ ID NO 5
<211> LENGTH: 32
<212> TYPE: PRT
<213> ORGANISM: Rat

<400> SEQUENCE: 5

Cys Gly Asn Leu Ser Thr Cys Met Leu Gly Thr Tyr Thr Gln Asp Leu
1               5                   10                  15

Asn Lys Phe His Thr Phe Pro Gln Thr Ser Ile Gly Val Gly Ala Pro
            20                  25                  30

<210> SEQ ID NO 6
<211> LENGTH: 32
<212> TYPE: PRT
<213> ORGANISM: Salmon

<400> SEQUENCE: 6

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```